United States Patent [19]

Cain et al.

[11] Patent Number: 5,368,044
[45] Date of Patent: Nov. 29, 1994

[54] VIBRATIONAL ANALYSIS OF BONES

[75] Inventors: Christopher M. J. Cain, Dulwich; Anthony P. Pohl, Marino, both of Australia

[73] Assignee: The Adelaide Bone and Joint Research Foundation, Inc., Adelaide, Australia

[21] Appl. No.: 849,417

[22] PCT Filed: Oct. 24, 1990

[86] PCT No.: PCT/AU90/00506

§ 371 Date: Apr. 24, 1992

§ 102(e) Date: Apr. 24, 1992

[87] PCT Pub. No.: WO91/06245

PCT Pub. Date: May 16, 1991

[30] Foreign Application Priority Data

Oct. 24, 1989 [AU] Australia ............................. PJ7036

[51] Int. Cl.$^5$ .............................................. A61B 5/103
[52] U.S. Cl. ..................................... 128/739; 128/774
[58] Field of Search ......................... 128/739, 773, 774; 73/579, 582, 588, 662; 324/635-636

[56] References Cited

U.S. PATENT DOCUMENTS 29,008  3/1875  Ott .
3,477,422  11/1969  Jurist .
4,754,763  7/1988  Doemland .
5,024,239  6/1990  Rosenstein .

FOREIGN PATENT DOCUMENTS 181131  5/1986  European Pat. Off. .
299906  1/1989  European Pat. Off. .
2156983  10/1985  United Kingdom .
8806882  9/1988  WIPO .
9001903  3/1990  WIPO .
9006720  6/1990  WIPO .

OTHER PUBLICATIONS

Sekigushi et al., "Assessment of fracture healing by vibration", Acta Orthrop. Scand. 1979, 50:391.
Van der Perre et al., "Identification of in vivo vibration modes of human tibia by model analysis", J. Biomechanics, vol. 105, pp. 224-248.
Vayo, "Wave propagation in bone media", Bulletin Math Biophy 1971, vol. 33, p. 463.
Brash et al., "Determination of the modulus of elasticity of bone by a vibration method", Med. Biol. Eng. 1970: 8:389.
Nokes et al., "Vibrations in Orthopedics", Critical Reviews in Biomedical Engineering.
Campbell et al., "Mechanical impedance of the femur: a preliminary report" J. Biomech 1971, vol. 4, pp. 319-322.
Christensen, "Resonance of Human Tibia Method Reproducibility and Effect of Transection", Acta Orthope Scand. 1982: 53:867.
Christensen et al., "Assessment of Tibial Stiffness By Vibration Testing In Situ.—I. Identification of Mode Shapes in Different Dupporting Conditions", J. Biomech 1986: vol. 19, No. 1, pp. 53-60.
Collier et al., "The Mechanical Mesponses of a Muman Tibia: Part 1—In Vitro", J. Biomech 1982, vol. 15, No. 15, No. 8, pp. 545-553.

(List continued on next page.)

Primary Examiner—Angela D. Sykes
Attorney, Agent, or Firm—Knobbe, Martens, Olson & Bear

[57] ABSTRACT

Method and apparatus for clinically recording and comparing the stiffness of a body element in-vivo. The body element, preferably a long bone (14) is excited by a vibratory device (15) and various vibrational resonant nodes are detected. Display or numerical analysis enables a comparison of the peak frequency response or a cross-correlation of the frequency versus amplitude response, thereby providing a measure of the state of stiffness of the body element compared with a normal or contralateral limb. The apparatus is simple to apply and use, ensuring effective use of method and apparatus in the clinical environment.

21 Claims, 5 Drawing Sheets

OTHER PUBLICATIONS

Cornelissen et al., "Assessment of Tibial Stiffness by Vibration Testing In Situ—II. Influence of Soft Tissues, Joints and Fibula", J. Biomech 1986, vol. 19, No. 7. pp. 551–561.

Cornelissen et al., "Assessment of Tibial Stiffness by Vibration Testing In Situ—III. Sensitivity of Different Modes and Interpretation of Vibration Measurements", J. Biomech. 1987, vol. 20. No. 4, pp. 333–342.

Denker et al., "Early Diagnosis of Interposition in Fractures with the Aid of a Vibrator", Acta Orthop Scand 1967: 38:396.

Doemland et al., "Assessment of Fracture Healing by Spectral Analysis", Journal of Medical Engineering & Technology, vol. 10, No. 4 pp. 180–187, 1986.

Doherty et al., "Evaluation of the use of Resonsant Frequencies to Characterise Physical Properties of Human Long Bones", J. Biomechanics, vol. 7, pp. 559–561, 1974.

Jurist, "In–vivo Determination of the Elastic Response of Bone I. Method of Ulnar Resonant Frequency Determination", Phys. Med. Biol. 1970, vol. 15, No. 3, p. 417.

Jurist et al., "Reproducibility of Ulnar Resonant Frequency Measurement", Aerospace Medicine, Aug. 1970, pp. 875–876.

Jurist et al., "Human Ulnar Bending Stiffness, Mineral Content, Geometry and Strength", Journal Biomechanics, 1977, vol. 10, pp. 455–459.

Jernberger, "A Method of Acoustic Registration of Fracture Healing", Acta Orthop Scand, 1967, 38:393.

Levine et al., "A Simplified Method of Attaching Accelerometer Packages to Bone", J. Biomechanics 1979, vol. 12, pp. 47–54.

Lewis, "A Dynamic Model of a Healed Fractured Long Bone" J. Biomechanics 1975, vol. 8, pp. 17–25.

Lippmann, "The Use of Auscultatory Percussion for the Examination of Fractures", J. Bone Joint Surgery 1932, vol. 14, p. 118.

Markey et al., "Tibial Resonant Frequency Measurements as an Index of the Strength of Fracture Union", Wisconsin Medical Journal, May 1974, vol. 73, pp. 62–65.

McGaw, "Osseosonometry", Arch. Surg. 1942, vol. 45, p. 195.

Moazedi et al., "Early Fracture-Strength Diagnosis Using Vibrational Testing", Proc. 35th Annual Meeting Orthopaedic Research Society, Feb. 1989, Las Vegas.

Nikiforidis et al., "Monitoring of Fracture Healing by Lateral and Axial Vibration Analysis", J. Biomechanics. 1990, vol. 23, pp. 323–330.

Nokes et al., "Direct and Indirect Determination of Tibial Natural Frequency—A Comparison of Frequency Domain Analysis and Fast Fourier Transformation", J. Biomedical Engineering 1984, vol. 6, p. 45.

Noyes et al., "Mechanical Input Impedance of Human Teeth In Vivo", Medical Biol. Eng. 1968, vol. 6, p. 487.

Orne, "The In Vivo Driving Point Impedance of the Human Ulna—A Viscoelastic Beam Model", J. Biomech. 1974, vol. 7, pp. 249–257.

Orne et al., "The Influence of Musculature on the Mechanical Impedance of the Human Ulna, an In Vivo Simulated Study", J. Biomech. 1975, vol. 8, pp. 143–149.

Orne et al., "The Effects of Variable Mass and Geometry, Pretwist, Shear Deformation and Rotatory Inertia on the Resonant Frequencies of Intact Long Bones: A Finite Element Model Analysis", J. Biomechanics 1976, vol. 9, pp. 763–770.

Pelker et al., "A Theoretical Investigation of Wave Propagation in Long Bones", American Society of Mechanical Engineers, New York 1975, p. 98.

Pelker et al., "Stress Wave Propagation in Bone", J. Biomechanics 1983, vol. 16, pp. 481–489.

Pelker et al., "Wave Propagation Across a Bony Discontinuity Simulating a Healing Fracture", J. Biomechanics, vol. 18, pp. 745–753.

Pugh, "Studies of the Impact Response of Human Limbs", Proc. 28th Annual Conference on Engineering in Medicine and Biology, Meeting New Orleans, Sep. 1975.

(List continued on next page.)

OTHER PUBLICATIONS

Saha et al., "The Effect on Soft Tissue on Wave-Propagation and Vibration Tests for Determining the In-Vivo Properties of Bone", J. Biomechanics 1977, vol. 10, pp. 393–401.

Jurist et al., "Acoustical Detection of Senile Osteoporosis", Proc. Soc. Bio. Med. 1966, 121:150.

Sonstegaard et al., "Sonic Diagnosis of Bone Fracture Healing—A Preliminary Study", J. Biomechanics 1976, vol. 9, pp. 689–694.

Streitman et al., "The Response of the Lower Extremity to Impact Forces", Bull Hosp. Joint Diseases, 1979, 39:120.

Thompson et al., "In Vivo Determinations of Mechanical Properties of the Human Ulna by Means of Mechanical Impedance Tests: Experimental Results and Improved Mathematical Models", Medical and Biological Engineering 1976, vol. 14, pp. 253–262.

Thomsen, "Modelling Human Tibia Structural Vibrations", J. Biomechanics 1990, vol. 23, pp. 215–228.

Vandecasteele et al., "Evaluation of Bone Strength and Integrity by Vibration Methods" Identification of In Vivo Excitated Modes, In Stokes, 1 AF, ed: Mechanical Factors and the skeleton. John Libbey 1981.

Wong et al., "The assessment of in viva bone condition in human by impact response measurement", J. Biomechanics 1983, vol. 16, No. 10, pp. 849–856.

VIBRATIONAL ANALYSIS OF BONES

This invention relates to a method and apparatus for the non-invasive evaluation of diseased or fractured bone, and in particular for identifying the structural integrity of long bones in-vivo.

BACKGROUND OF THE INVENTION

At present the clinician decides when the injured or diseased bone can resume normal unsupported function on the basis of physical examination, radiographs, the passage of time and patient evaluation of pain as a result of stress placed on the bone.

Vibrational analysis of bones has been used in the experimental environment for the examination of diseased and fractured bones and pathological orthopaedic disorders however the primary reason for the lack of acceptance of this method of bone analysis by clinicians has been the lack of reliability of the results. Most importantly the clinician has not been able to reliably assess from the results of tests when and if the bone under examination has regained structural integrity.

The lack of reliability and reproducibility of the prior vibrational analysis methods result from a number of factors identified by the inventors. These factors include insufficient range of excitation frequency, inappropriate excitation means, inconsistent detection and methodology of measurement, a lack of appreciation of the need to assess more than just one mode of excitation and the choice of unnecessarily complicated stiffness criteria for clinical evaluation.

Also of importance is the method of support provided to the bone under examination and the assessment of the effects of external or internal fixation devices which both contribute to the accuracy, reproducibility and practical clinical use of prior analysis methods and means.

BRIEF SUMMARY OF THE INVENTION

Therefore this invention aims to overcome the aforementioned problems and provide a method and apparatus suitable for use by clinicians primarily for the in-vivo monitoring of bone fracture healing but which may also be used for the assessment of other pathological bone conditions such as but not confined to osteoporosis, primary and secondary tumour deposits, other bone lesions, other bones and other bodily beam like structures such as teeth.

Preferably the apparatus comprises simple elements that are quick to apply and by adherence to the method of the invention, provides reliable, reproducible and accurate results which are consistent with empirical clinical evaluations of the structural integrity of the body element under examination by a method of comparison with a normal or contralateral body element.

In its broadest form, the invention is directed to a method for applying in-vivo a non-invasive vibrational motion to a selected fractured or diseased body element for determining the stiffness state of the selected body element, said method comprising the steps of: a) placing a vibration transducer means in firm mechanical contact with the selected element at an end region thereof for detecting vibratory energy, b) contacting a vibratory device against the selected element at a first location remote from said end region, c) driving the said vibratory device to vibrate over a frequency range between 20 to 2,000 Hertz at a predetermined rate of frequency change, d) using a computer device to store a first mode of vibratory response from the vibration transducer means, e) contacting the vibratory device against the selected element at a second location also remote from said end region, f) repeating steps c) and d) so as to store a second mode of vibratory response from said vibration transducer means, and g) producing a visual display for determining the difference between the peak frequency of each response mode and that of a corresponding reference mode representative of the stiffness of a normal body element to provide an indication of the stiffness state of the selected body element.

BRIEF DESCRIPTION OF THE DRAWINGS

In order that the invention may be clearly understood and readily carried into effect, a preferred embodiment will now be described by way of example only with reference to the accompanying representations, wherein.

DETAILED DESCRIPTION OF THE INVENTION

Figure 1:
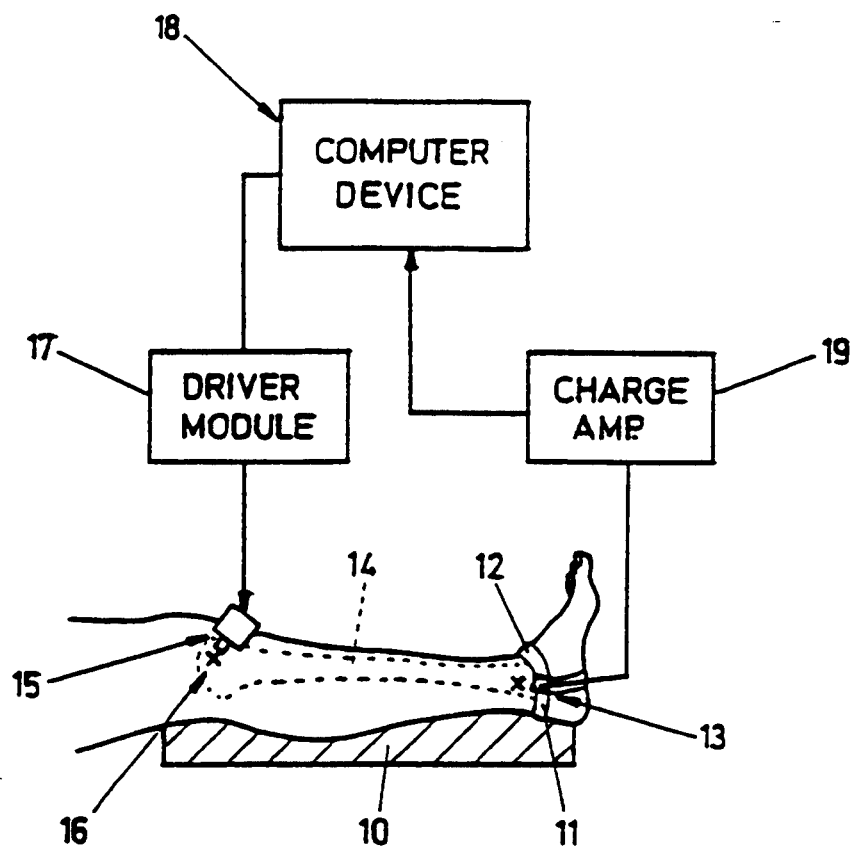
FIG. 1 depicts an embodiment of the apparatus of the invention in clinical use to measure the stiffness characteristics of a tibia in-vivo.

The apparatus as shown in FIG. 1 can be applied to any accessible body element, for example teeth, soft tissue, finger bones and in particular for the purpose of this description any long bone and for ease of description, the method and apparatus will be shown as applied to the tibia but is equally applicable to other bones such as the femur, humerus, radius and ulna.

Regardless of the bone to be examined it is preferable that it be supported so that the part of the limb under study has reduced constraint from effects of the body's linkages of that limb to other parts of the body and places the surrounding muscle and tissue into a relaxed state.

In this embodiment a cushion at 10 in FIG. 1 supports the upper leg at the knee with both hip and knee slightly flexed thus relaxing the muscles adjacent the knee joint. When the lower leg, particularly the tibia, is supported by the body of the cushion, the heel is likewise supported allowing the foot itself to assume a relaxed posture and thereby relaxing muscle and tissue adjacent the ankle joint. Support of the leg in this fashion allows the tibia to approach an unbound state. In this embodiment a unitary sculptured cushion is used to provide the required support.

The following steps comprise a method of measurement and analysis which is applicable to either normal or injured limbs. When comparisons are made the reference data used in the method may consist of data collected from a) measurements made on a normal contralateral limb of the same patient or b) data representative of the most likely equivalent element which may be compiled from a number of other patients or inferred from the bone being examined.

Step A comprises the placement of the vibration transducer. General guidelines are applicable in relation to this step wherein choice of location requires that there exist least possible depths of skin and subcutaneous tissue between the transducer and the bone under examination, generally referred to as the most prominent subcutaneous point of the bone. This is preferably located at or near the end regions of the bone and in the example of a fractured bone at least at opposite sides of the fracture. In this embodiment the medial malleolus of the distal region of the tibia is the most ideal location for the vibration transducer.

FIG. 1 depicts the vibration transducer which in this embodiment is a Bruel and Kjaer 4382 accelerometer 11 having a compliant strap 12 located upon the medial malleolus 13 of the distal end region of the tibia 14. It is important that the accelerometer is palpably in the firmest contact with the bone underlying the soft tissue and the accelerometer position is maintained constant during the examination. The strap 12 must be comfortably compliant to the shape of the patient's ankle but must also retain the accelerometer in its position and orientation. It will be apparent that the accelerometer has been located such as to primarily detect vibrational energy acting in the medio-lateral plane of the tibia.

Figure 2:
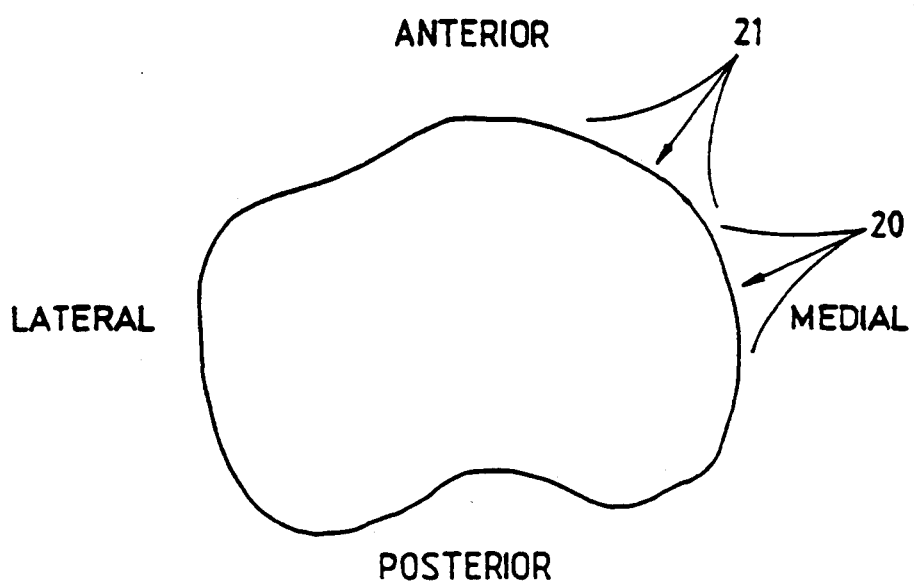
FIG. 2 depicts a cross section of the proximal end region of the tibia and indicates the preferable locations for application of a vibratory device.

Step B comprises the placement of the vibration device in accordance with the previously described guidelines to detect a first mode of resonant vibration of the bone. The vibratory device 15 in this embodiment is a Bruel and Kjaer vibration exciter model 4310 and is first located on the medial surface of the medial tibial plateau 16 of the proximal end region of the tibia 14. This first location is also displayed as 20 in FIG. 2.

Figure 7:
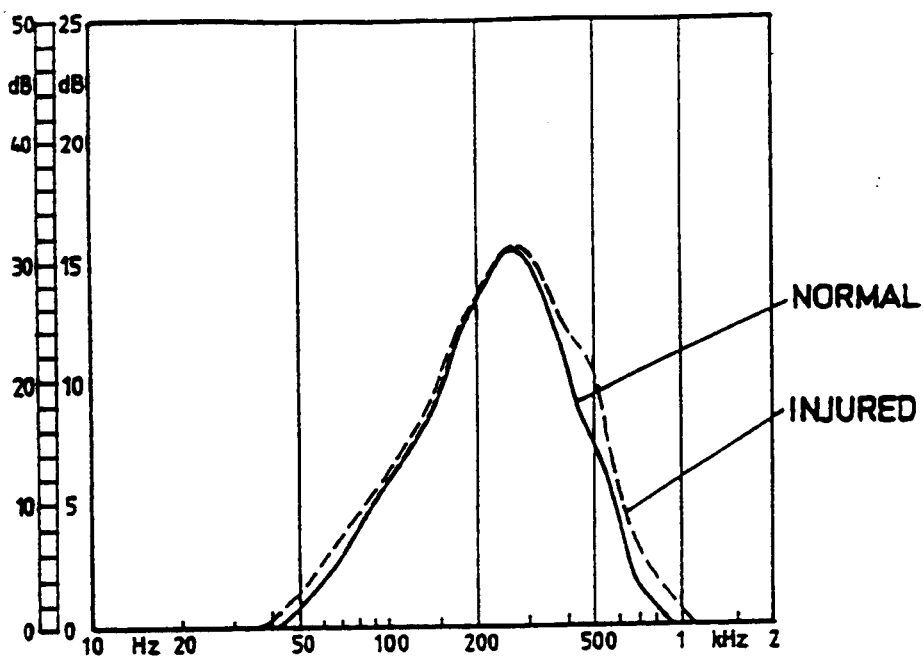
FIG. 7 shows a typical graphical representation of the resonance characteristics of a healed tibial fracture and that of a normal contralateral bone for the first mode of resonance.

In this location the vibratory energy imparted is in a medio-lateral plane of the tibia. FIG. 7 depicts an embodiment of the vibration exciter which has been adapted for hand-held operation. Incorporated into the vibration exciter is a spring tensioned mechanical preload means which ensures that each user applies a consistent pressure lying between a predetermined range of 1 to 20 Newtons.

Step C comprises driving the vibratory device. The vibration exciter is driven by a constant amplitude sinusoidal wave form provided by a driver module 17 which is controlled by a voltage signal supplied by a digital to analogue output of a computer device 18. The frequency excursion of the sinusoidal wave form comprises a linear (or alternatively a logarithmic) sweep from 20 Hz to 2,000 Hz over a period of time between 2 to 30 seconds.

Step D comprises storing the vibratory response of the tibia. Vibratory response of the tibia is detected by the accelerometer 11 which is connected to a charge amplifier. The charge amplifier amplifies the electrical signal output of the accelerometer and converts the signal into a varying analogue voltage suitable for connection to the analogue to digital input of a computer device 18 which is then stored for recall or further processing as required.

Figure 4:
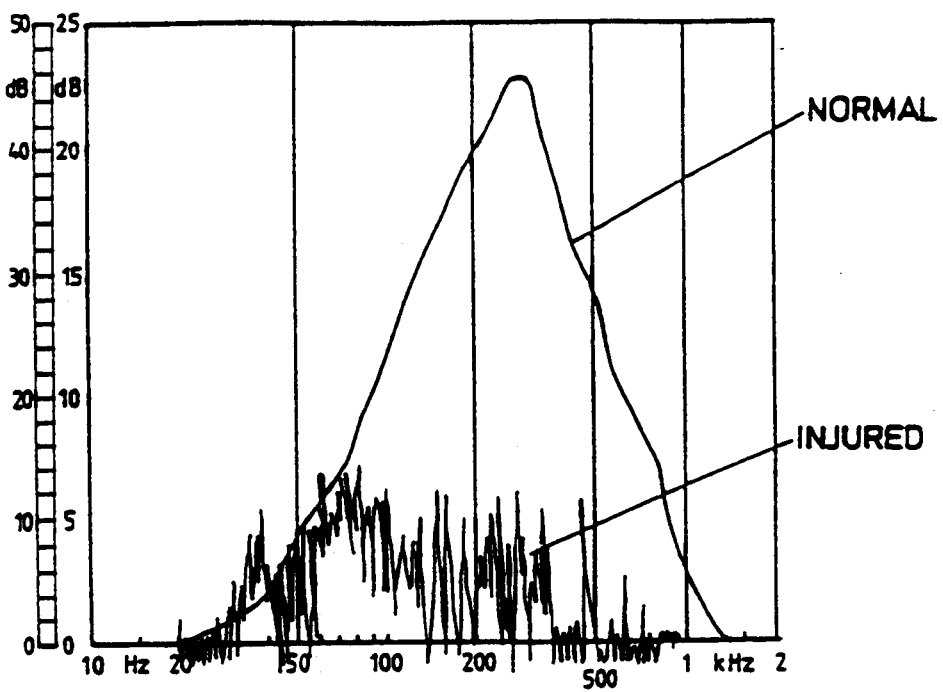
FIG. 4 depicts an example of the output of a chart recording which displays the resonance characteristics of a first mode of resonance of an injured and contralateral normal tibia.
Figure 5:
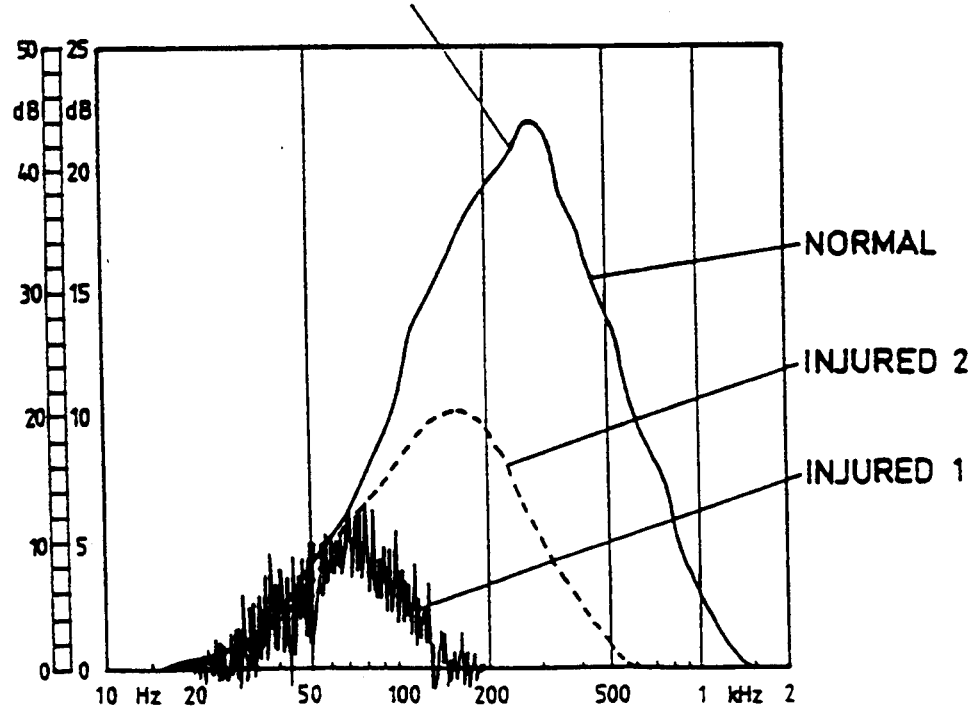
FIG. 5 depicts an example of the output of a chart recording of a first mode of resonance of a bone during the union process.
Figure 6:
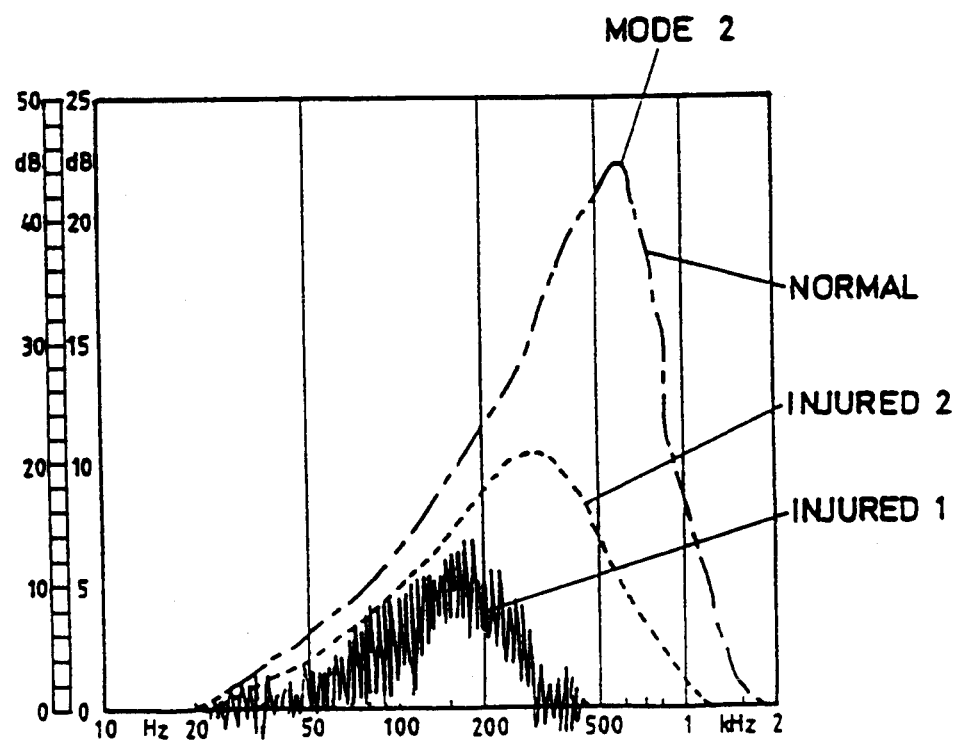
FIG. 6 depicts an example of the output of a chart recording of a second mode of resonance of a bone during the union process.

This signal may then be displayed as a first vibratory response on a plotter and or a visual display screen. In this embodiment an amplitude versus frequency plot of the vibratory response is provided, an example of which is shown in FIGS. 4-6. It is the frequency of the peak of the response which provides the most relevant stiffness characteristic of the limb under examination and is generally referred to as modal response of the bone under examination. A well defined peak is an ideal modal response while a indistinguishable peak frequency response is a non-ideal modal response.

It is not unusual for these steps to be repeated to provide the clinician the opportunity to vary the location of the vibratory device at points located across the region in a plane orthogonal to the longitudinal axis of body element under examination. This step may provide a series of displays which exhibit in most instances a single peaked response and it is important that the clinician obtain the smoothest and most clearly peaked response possible representative of an ideal modal response from the bone under examination.

An ancillary parameter is that of amplitude which is purely relative to the amplitude of the driving signal provided to the vibratory device. This parameter can be controlled by the clinician to ensure that the peak is of sufficient prominence for assessment of its frequency value but need not be any greater. However, it is important to have a similar amplitude response when comparisons of the contralateral results are made so as to simplify statistical analysis.

Step E then comprises the placement of the vibratory device to detect a second mode of resonant vibration. This secondary mode will be generated as a result of applying the vibratory energy on a different location of the proximal region of the tibia. This second mode will be found in most long and short beam like members of the body, particularly long bones and is now understood to be a second flexural mode of resonance.

Of particular import to this invention is that it is now recognised that both modes of resonance need to exhibit normal responses within acceptable variance before proper union or repair of diseased bone can be said to have occurred.

In this embodiment the vibratory device is then located on a second proximal end region of the tibia 14 at the anteromedial surface of the medial tibial plateau. This second location is also displayed as 21 in FIG. 2. The previously described signals are provided to drive the vibratory device.

The vibratory device preferably applies its vibrational energy in a plane which lies at an acute angle to the medial lateral plane.

The signal output of the accelerometer is stored and displayed as a second mode of vibratory response.

As previously described it is not unusual for this step to be repeated until a consistent single peaked response is obtained which will have a peak frequency higher than that obtained for the location chosen for Step B. Due allowance is made over the period of union of a fractured bone for the alteration of muscle tone and the like which is likely to marginally affect the amplitude response, but, in general not affect the peak frequency detected.

The described method of modal response measurement is also used to store the stiffness characteristics of a normal bone. In the given example the contralateral tibia is used although a modal response representative of a comparable tibia may suffice.

Indeed the contralateral tibia of a person may have a slight variance from its pair even before it was fractured or diseased so the comparison yet to be performed between the results will account for this expected variance.

Step G compares in the first instance of this embodiment the peak frequency of the measured results. Comparison of the modal response may be achieved in a number of ways. Most convenient and of simpler implementation is the method of comparing the peak frequency of each mode with the corresponding contralateral mode and if both comparisons fall within a predetermined range, the stiffness of the bones are similar and the clinician can be confident that the bones are comparably stiff.

Alternatively, a statistical analysis of the recorded modal responses, may be conducted to produce a correlation coefficient which if for each mode is within a predetermined range will likewise indicate to the clinician that the stiffness of the bones are similar.

It is important that both modes of vibratory response are detected and their comparisons fall within the predetermined range since one without the other indicates from physical examination that normal stiffness has not yet been achieved.

Step H is the first in a series of additional steps that provide further assurance to the clinician that the bones under comparison are comparably stiff. The placement of the vibratory device is relocated to detect a third mode of resonant vibration. This third mode may not be found in all bones or indeed in every body element however it is recognised in the tibia as being a torsional mode of resonance which generally occurs at a higher frequency than the previously discussed flexural modes of resonance.

The tibial example indicates that the anterior surface of the tibial tuberosity is the preferred location for detecting the third mode of resonance.

Steps I, J and K are identical to steps C, D and G as previously discussed.

Figure 3:
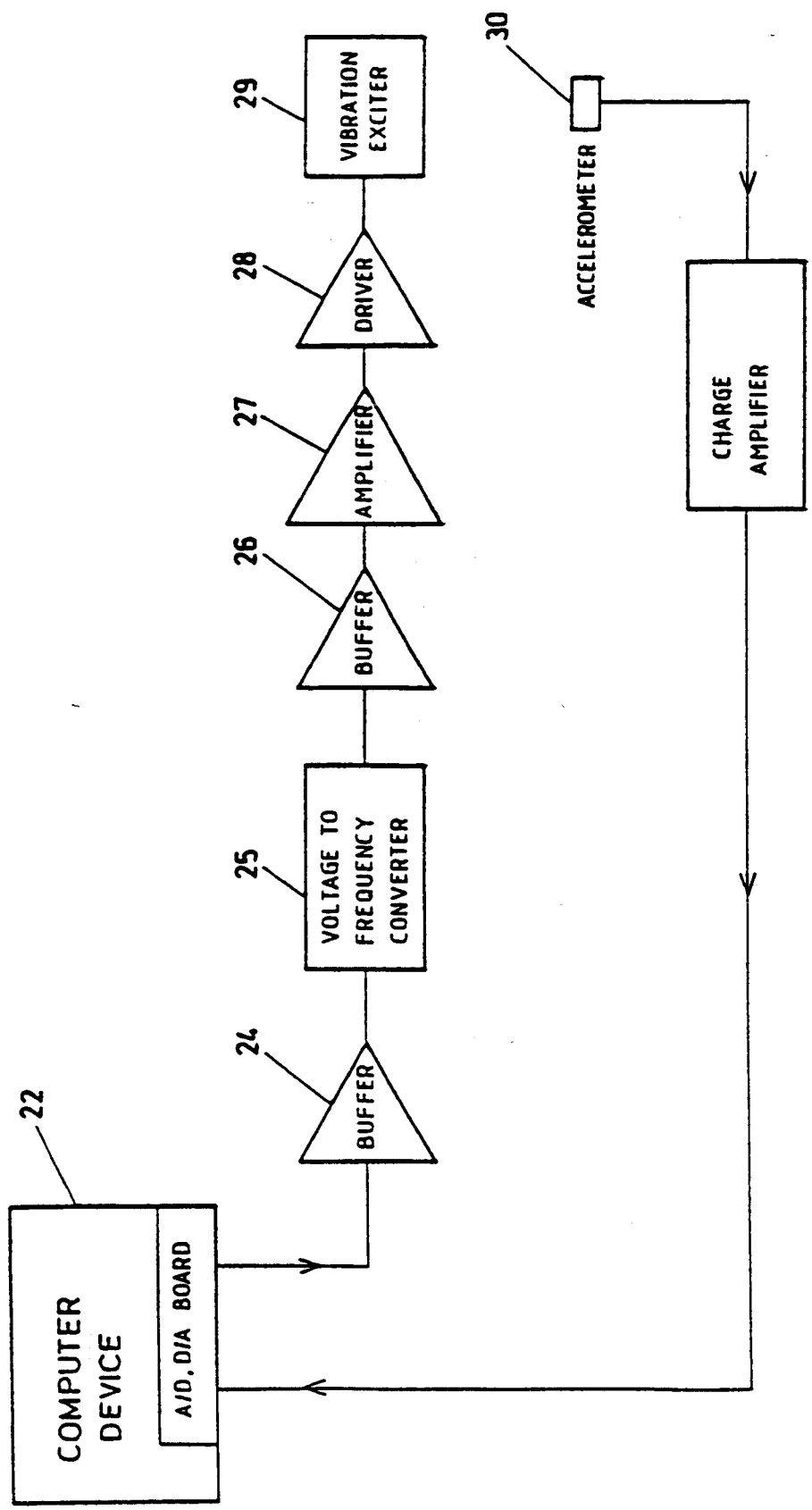
FIG. 3 depicts a functional block diagram of the apparatus of an embodiment of the invention.

FIG. 3 depicts an embodiment of a functional block diagram of an apparatus suitable for implementation of the invention. The circuits which comprise the function blocks are of a well known nature and require no further description. It will be apparent that these circuits may be variously configured, wherein, for example the computer device 22 may contain within its housing on standard plug compatible cards, the charge amplifier 23 and/or the circuit modules 23–28, while the vibration exciter 29 and the accelerometer 30 are simply plugged into external connector sockets, thereby providing an exceedingly simple arrangement for clinical use.

FIG. 4 depicts an example of the output of a chart recorder showing a logarithmic display of frequency along the x-axis and relative amplitude along the y-axis. The trace shown as "Normal" indicates the typical frequency to amplitude characteristics of the patients un-injured or ostensibly normal bone, indicating by its smooth transition and clear peak that the bone has a first modal resonance of approximately 260 Hz. The method of the embodiment shown has exhibited an accuracy of ±5 Hz even when applied by different clinicians.

In comparison the trace shown as "INJURED" typically indicates the frequency to amplitude characteristics of an acutely injured bone, indicated by its irregular and imprecise frequency. Its frequency and amplitude however, is recognisably lower and is determined by averaging the frequency of maximal amplitude response over consecutive measurements which in this case is approximately 84 Hz. Normal clinical tests confirmed that the injured bone had no evidence of significant bony union.

It has been found that in general, acutely fractured bones exhibit an irregular, low frequency resonance usually below 100 Hz whereas un-injured or united bone exhibits a resonance between 200 Hz and 500 Hz and typically about 350 Hz for a normal adult male and 300 Hz for normal adult female. It has been found that the shape of the normal response curve is typical for each individual and that the frequency at peak amplitude response (resonance) remains constant for that individual.

Measured resonance characteristics of bone are generally unaffected by the presence of surgical nails, screws, plates and pins. It is found that the resonance of these devices is usually easily identifiable as a discrete lesser amplitude peak than that of the excitation response of a bone under examination and their contribution becomes less noticeable as the bone union develops. Thus it is found that the characteristic resonance of united bone resembles that of the normal contralateral limb even with the internal or external fixation devices in place.

FIG. 5 shows a typical graphical representation of the first modal resonance characteristics of a fractured bone. The modal response showing an irregular trace "INJURED 1" exhibits a low peak amplitude value and a lower frequency of resonance of 84 Hz four weeks after the injury. The intermediate stage of bone union is depicted as "INJURED 2" eight weeks after injury which has a more regular trace, an increased amplitude and a higher resonant frequency of 148 Hz. This indicates union is progressing and the stiffness of the bone union has improved although has not yet reached that expected of a contralateral normal limb. The trace denoted "NORMAL" which has a regular shape exhibiting, the greatest amplitude and a resonant frequency of 260 Hz.

FIG. 6 shows a corresponding second modal resonance characteristic of the same fractured bone described in FIG. 5. The peak resonances of each trace are correspondingly higher than those of FIG. 5 and are characteristic of this second flexural mode of the bone.

FIG. 7 shows a typical graphical representation of the resonance characteristics of a healed tibial fracture and that of a normal contralateral bone using the first modal response as an example.

The concordance of these traces and their peak frequencies provides confirmation to the clinician that bone union has occurred and that it has sufficient stiffness to resume normal activity.

It has been found by using the invention that an average variation of the resonance value between normal contralateral limbs is 2.9% with a maximum acceptable variation of 8.0%.

Although abnormal variation between contralateral limbs has not been found in elderly persons, allowance for typical normal resonance values needs to be made for the bones of elderly persons. It has been found that the lower density of bones caused by age and osteoporosis results in a lower resonant frequency than would be expected by limb length and circumstance. However this characteristic is consistent, resulting in a response which has a sharp and well defined peak, such that comparison to fractured or diseased bone is still possible and the method and apparatus still applicable to their assessment.

Likewise the resonance will shift downwards by a predictable amount where the limb has become shortened as a result of the fracture and healing process.

Figure 8:
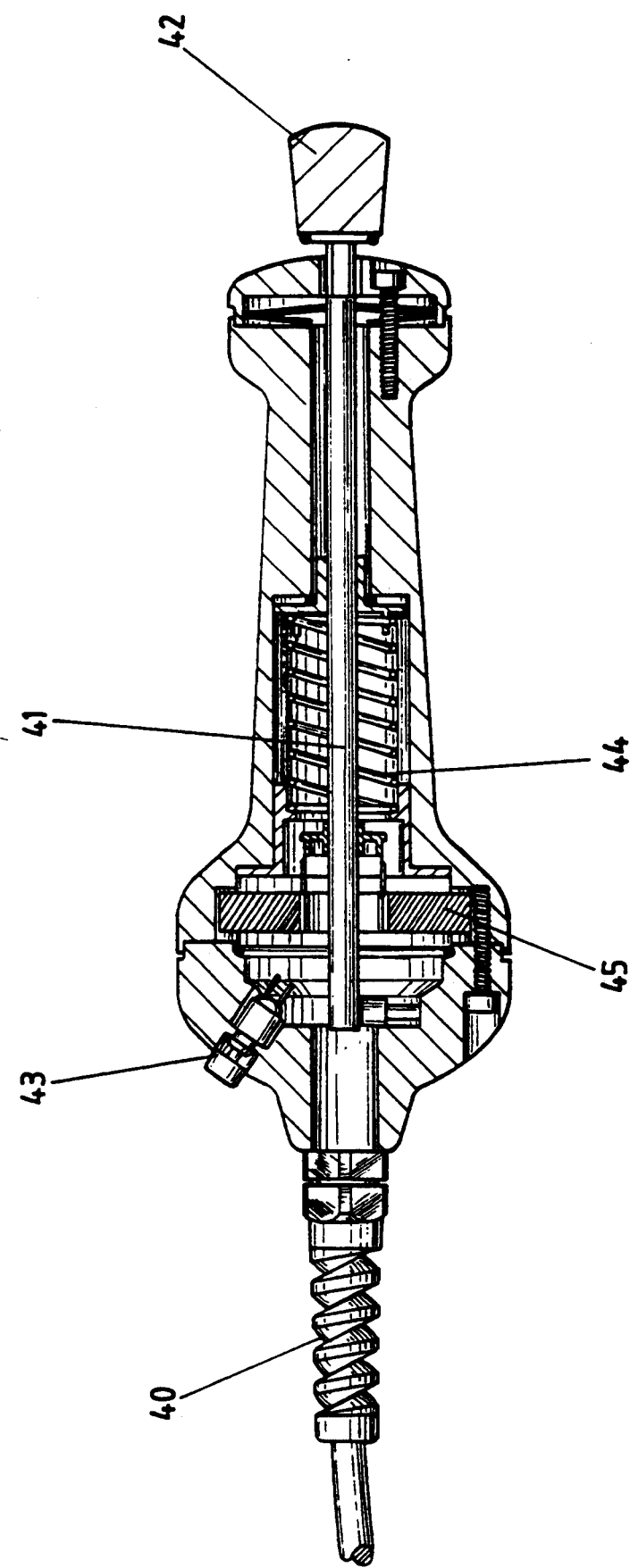
FIG. 8 depicts an embodiment of the vibration device.

FIG. 8 depicts an embodiment of the vibration device, which as previously described, comprises a voice coil and magnet vibration exciter 15. To effect ease of handling and application to the patient, the vibration device has been modelled into the shape shown in plan view in FIG. 8, which however is indicative of its substantially cylindrical shape.

Wires supplying motive energy enter the body of the device via stress relief member 40 and connect to the encased exciter 45 in the normal manner. Shaft 41 is the reciprocating member of the device and its head 42 is the portion of the device which is applied to the bone or body member under examination. A spring 44 is arranged with its longitudinal axis coaxial with the shaft 41 and provides a predetermined pre-load force when the head is applied to the body. A pre-load force of between 1 to 20 Newtons has been found adequate for energy transference and also comfortable for patients.

When applying the method of the invention it is convenient for the clinician to initiate the step of driving the vibratory device when it has been firmly located on the body. Thus, switch 43 is located in easy reach of the thumb of the hand holding the vibratory device. Alternatively, the step of driving the device may be automatically repeated by the computer device until a suitable trace of resonant response is obtained and its results stored for analysis.

This invention therefore provides a reliable and accurate clinical tool for non-invasive assessment of diseased or fractured bone in-vivo.

We claim:

1. A method for applying in-vivo a non-invasive vibrational motion to a selected fractured or diseased body element for determining the stiffness state of the selected body element, said method comprising the steps of:
   a) placing a vibration transducer means in firm mechanical contact with the selected element at an end region thereof for detecting vibratory energy,
   b) contacting a vibratory device against the selected element at a first location remote from said end region,
   c) driving the said vibratory device to vibrate over a frequency range between 20 to 2,000 Hertz at a predetermined rate of frequency change,
   d) using a computer device to store a first mode of vibratory response from the vibration transducer means,
   e) contacting the vibratory device against the selected element at a second location also remote from said end region,
   f) repeating steps c) and d) so as to store a second mode of vibratory response from said vibration transducer means, and
   g) producing a visual display for determining the difference between the peak frequency of each response mode and that of a corresponding reference mode representative of the stiffness of a normal body element to provide an indication of the stiffness state of the selected body element.

2. The method of claim 1 further comprising the steps of:
   h) contacting a vibratory device against the selected element at a third location also remote from said end region,
   i) driving the said vibratory device to vibrate over a frequency range between 20 to 2,000 Hertz at a predetermined rate of frequency change,
   j) using a computer device to store a third mode of vibratory response from the vibration transducer means, and
   k) comparing the stored responses of all three modes with corresponding stored reference mode responses.

3. The method of claim 1 or claim 2 wherein the difference between the peak frequency of each response mode with a corresponding reference mode lies within a predetermined range.

4. The method of claim 1 or claim 2 wherein a correlation of corresponding portions of the response modes with the corresponding reference modes provides a correlation coefficient within a predetermined range to indicate clinically acceptable equivalence of the stiffness of the body element and the reference mode.

5. The method of claim 2 wherein the third location is the anterior surface of the tribal tuberosity.

6. The method of claim 1 wherein said selected body element is long bone.

7. The method of claim 6 wherein the said long bone is the tibia and the vibration transducer means is in firm mechanical contact with the medial malleolus.

8. The method of claim 7 wherein the first location is the medial surface of the medial tibial plateau and the vibratory device applies its energy in the medial-lateral plane.

9. The method of claim 7 wherein the second location is the anteromedial surface of the medial tibial plateau and the vibratory device applies its energy in a plane at an acute angle to the medial-lateral plane.

10. The method of claim 1 wherein the selected body element is supported along its length by a unitary support cushion.

11. The method of claim 1 further comprising the step of displaying the first and second mode of vibratory response and their corresponding reference modes.

12. The method of claim 11 further comprising the step of displaying a visual representation of the amplitude of the vibration transducer signal versus the frequency applied to the vibratory device.

13. The method of claim 12 further comprising the step of displaying the peak frequency of said visual representation.

14. The method of claim 1 wherein the vibratory device is applied at points across a respective said location in a plane orthogonal to the longitudinal axis of the selected body element until the displayed vibratory response comprises a single peak.

15. Apparatus for applying in-vivo a non-invasive vibrational motion to a selected fractured or diseased body element for determining the stiffness state of the selected body element, said apparatus comprising:
   a vibration transducer means arranged to be applied to the selected body element at an end region thereof having a signal output representing a response mode of vibration of the selected element having a peak frequency,
   a vibratory device adapted to be applied to the selected body element at a location remote from said end region of said selected body element,
   computer means comprising signal output means to drive the vibratory device to vibrate over a frequency range between 20 to 2,000 hertz at a predetermined rate of frequency change, storage means having stored therein a plurality of reference vibration transducer response modes having a peak frequency representative of the stiffness of a normal body element, and comparison means adapted to produce a visual display for determining the difference between the peak frequency of the vibration transducer response mode and that of a corresponding stored response mode to provide an indication of the stiffness state of the selected body element.

16. The apparatus of claim 15 wherein said comparison means determines if the difference between the peak frequency of each response mode with a corresponding reference mode lies within a predetermined range.

17. Apparatus according to claim 15 wherein said comparison means correlates corresponding portions of the response and reference modes to provide a numerical correlation coefficient which if within a predetermined range indicates a clinically acceptable equivalence of the stiffness of the selected body element and the normal body element.

18. Apparatus according to claim 17 wherein the vibratory device has a substantially elongate outer shape adapted for holding by the hand, having a coaxial vibrating member therein, an external portion of the vibrating member being adapted for firmly applying vibratory energy to a selected body element and preload means therein.

19. Apparatus according to claim 15 wherein the comparison means comprises a visual display of the signal output from the vibration transducer and the reference mode.

20. Apparatus according to claim 19 wherein the visual display comprises a graphical representation of an amplitude to frequency response of the signal output of the vibration transducer superimposed onto the reference vibrational response mode.

21. Apparatus according to claim 15 wherein the vibratory device comprises a hand held electromechanical shaker having a switch operable to initiate operation of the signal output means.

* * * * *